United States Patent
Selvaraj et al.

(10) Patent No.: US 11,607,138 B2
(45) Date of Patent: Mar. 21, 2023

(54) RESPIRATORY RATE DETECTION USING DECOMPOSITION OF ECG

(71) Applicant: Vital Connect, Inc., San Jose, CA (US)

(72) Inventors: Nandakumar Selvaraj, Santa Clara, CA (US); Ravi Narasimhan, Sunnyvale, CA (US)

(73) Assignee: Vital Connect, Inc., San Jose, CA (US)

(*) Notice: Subject to any disclaimer, the term of this patent is extended or adjusted under 35 U.S.C. 154(b) by 187 days.

(21) Appl. No.: 16/516,534

(22) Filed: Jul. 19, 2019

(65) Prior Publication Data
US 2019/0336010 A1 Nov. 7, 2019

Related U.S. Application Data

(62) Division of application No. 13/487,022, filed on Jun. 1, 2012, now Pat. No. 10,357,163.

(51) Int. Cl.
*A61B 5/0205* (2006.01)
*A61B 5/08* (2006.01)
*A61B 5/318* (2021.01)
*A61B 5/00* (2006.01)

(52) U.S. Cl.
CPC ......... *A61B 5/0205* (2013.01); *A61B 5/0816* (2013.01); *A61B 5/318* (2021.01); *A61B 5/7235* (2013.01)

(58) Field of Classification Search
CPC ..... A61B 5/0205; A61B 5/318; A61B 5/0816; A61B 5/7235; A61B 5/282; A61B 5/7257; A61B 5/7207; A61B 5/7278
See application file for complete search history.

(56) References Cited

U.S. PATENT DOCUMENTS

| | | | |
|---|---|---|---|
| 8,660,848 B1* | 2/2014 | Humi | G01V 1/008 704/270 |
| 2002/0045836 A1 | 4/2002 | Alkawwas | |
| 2006/0178591 A1 | 8/2006 | Hempfling | |
| 2010/0125213 A1* | 5/2010 | Lo | A61B 5/021 600/500 |

(Continued)

FOREIGN PATENT DOCUMENTS

WO   WO-2012036135 A1 *  3/2012 ............ A61B 5/112

OTHER PUBLICATIONS

M. Campolo, D. Labate, F. La Foresta, F. C. Morabito, A. Lay-Ekuakille and P. Vergallo, "ECG-derived respiratory signal using Empirical Mode Decomposition," 2011 IEEE International Symposium on Medical Measurements and Applications, 2011, pp. 399-403, doi: 10.1109/MeMeA.2011.5966727. (Year: 2011).*

(Continued)

*Primary Examiner* — Daniel L Cerioni
*Assistant Examiner* — Jonathan E. Cooper
(74) *Attorney, Agent, or Firm* — Brundidge & Stanger, P.C.

(57) ABSTRACT

A method and system for determining a respiratory rate of a user using an electrocardiogram (ECG) segment of the user are disclosed. The method comprises decomposing the ECG segment into a plurality of functions and evaluating the plurality of functions to choose one of the plurality of functions based on a respiratory band power. The method includes determining the respiratory rate using the one of the plurality of functions and a domain detection.

16 Claims, 7 Drawing Sheets

(56) References Cited

U.S. PATENT DOCUMENTS

| | | | | |
|---|---|---|---|---|
| 2011/0257556 | A1* | 10/2011 | Guo | A61B 5/4812 |
| | | | | 600/544 |
| 2013/0041277 | A1* | 2/2013 | Hsiao | A61B 5/087 |
| | | | | 600/529 |
| 2014/0180036 | A1* | 6/2014 | Bukkapatnam | A61B 5/0816 |
| | | | | 128/845 |

OTHER PUBLICATIONS

Madhav, et al. "Estimating of Respiration Rate from ECG, BP and PPG signals from Empirical Mode Decomposition." Instrumentation and Measurement Technology Conference. 2011 IEEE. pp. 1-4.
Chang, Kang,—Ming. "Arrhythmia ECG Noise Reduction by Ensemble Empirical Mode Decomposition." Sensors. 2010. pp. 6063-6080.
Balocchi, et al. "Deriving the respiratory sinus arrhythmia from the heartbeat time series using empirical mode decomposition." Chaos, Solitons, and Fractals. 2004. pp. 171-177.
Bu et al. "Monitoring of Respiration and Heartbeat during Sleep using a Flexible Piezoelectric Film Sensor and Empirical Mode Decomposition." IEEE. 2007. pp. 1362-1366.

* cited by examiner

RESPIRATORY RATE DETECTION USING DECOMPOSITION OF ECG

This application is a Divisional of U.S. application Ser. No. 13/487,022, filed Jun. 1, 2012, which is incorporated herein by reference in its entirety.

FIELD OF THE INVENTION

The present invention relates to sensor devices, and more particularly, to a sensor device utilized to determine respiratory rate using decomposition of an ECG.

BACKGROUND

A person's respiratory rate measures the number of breaths taken within a predetermined time period, typically 60 seconds. The respiration rate is one of the vital signs commonly used in clinical practices. Several pathological conditions such as sleep apnea and chronic obstructive pulmonary disease are associated with respiratory dysfunction and/or abnormal respiratory patterns. A person's age, physical condition, and medical history all have a direct effect on the ability to maintain a normal respiratory rate. Precise monitoring of a person's respiratory rate is crucial to identifying potential markers in the person's diagnosis and prognosis in various clinical settings.

Conventional methods of respiratory rate measurements include listening to lung sounds using stethoscopes, spirometry, capnography, inductance plethysomography, impedance pneumography, and thermistors. The drawbacks of these conventional methods include being expensive, invasive, cumbersome, inefficient, and inaccurate. In addition, these intrusive devices also interfere with natural physiological breathing patterns. Moreover, these conventional methods, while suitable for point-of-care applications, are not suitable for remote sensing, telehealth monitoring, and home-based, long-term monitoring applications.

These issues limit the continuous remote monitoring of a person's respiratory rate. Therefore, there is a strong need for a cost-effective solution that overcomes the above issues by non-invasively calculating respiratory rate in real-time using sensor devices. The present invention addresses such a need.

SUMMARY OF THE INVENTION

A method and system for determining a respiratory rate of a user using an electrocardiogram (ECG) segment of the user are disclosed. The method comprises decomposing the ECG segment into a plurality of functions and evaluating the plurality of functions to choose one of the plurality of functions based on a respiratory band power. The method includes determining the respiratory rate using the one of the plurality of functions and a domain detection.

In a second aspect, the system comprises a wireless sensor device with a processor and a memory device coupled to the processor, wherein the memory device stores an application which, when executed by the processor, causes the processor to decompose the ECG segment into a plurality of functions and to evaluate the plurality of functions to choose one of the plurality of functions based on a respiratory band power. The application further causes the processor to determine the respiratory rate using the one of the plurality of functions and a domain detection.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to sensor devices, and more particularly, to a sensor device utilized to determine respiratory rate using decomposition of an electrocardiogram (ECG). The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention allows for the measurement of a user's respiratory rate using a sensor device via decomposition of an ECG data signal segment. By connecting a sensor device to the user through two or more skin contacting sensor nodes or electrodes, an ECG data signal segment of the user can be measured. The ECG data signal segment is then processed to eliminate artifacts and noise and decomposed into Intrinsic Mode Functions (IMFs) using Ensemble Empirical Mode Decomposition (EEMD). These IMFs are evaluated and based upon a spectral content of the respiratory band power, the respiratory rate of the user is determined using time and frequency domains.

One of ordinary skill in the art readily recognizes that a variety of sensor devices can be utilized for the measuring of the ECG data signal segment including portable wireless sensor devices with embedded circuitry in a patch form factor and that would be within the spirit and scope of the present invention.

To describe the features of the present invention in more detail, refer now to the following description in conjunction with the accompanying Figures.

Figure 1:
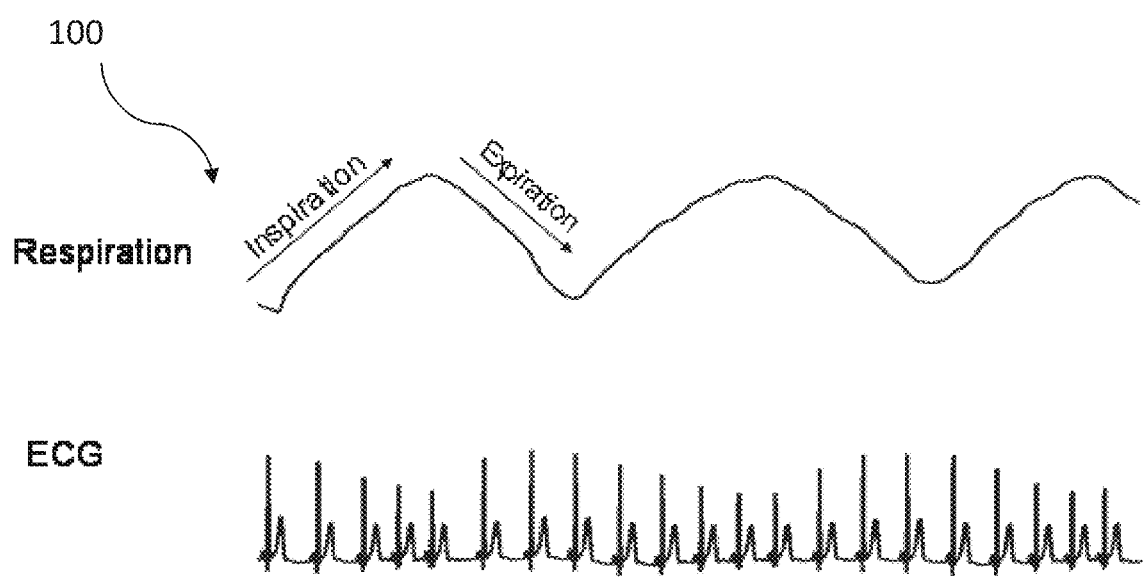
FIG. 1 illustrates a diagram of the respiratory effects on the ECG in accordance with an embodiment.

FIG. 1 illustrates a diagram 100 of the respiratory effects on the ECG in accordance with an embodiment. One of ordinary skill in the art readily recognizes that in addition to decomposition of the ECG data signal segment, a variety of ECG based algorithms can be utilized to measure the respiratory effects on the ECG including but not limited to band pass filtering, analyzing the QRS area, R amplitude, RS amplitude, and heart rate variability and that would be within the spirit and scope of the present invention. These ECG based algorithms require higher sampling rates of at least 500 Hertz (Hz) and are limited by the robustness of the R wave detection and the presence of pacemakers and/or abnormal heart rhythms.

Figure 2:
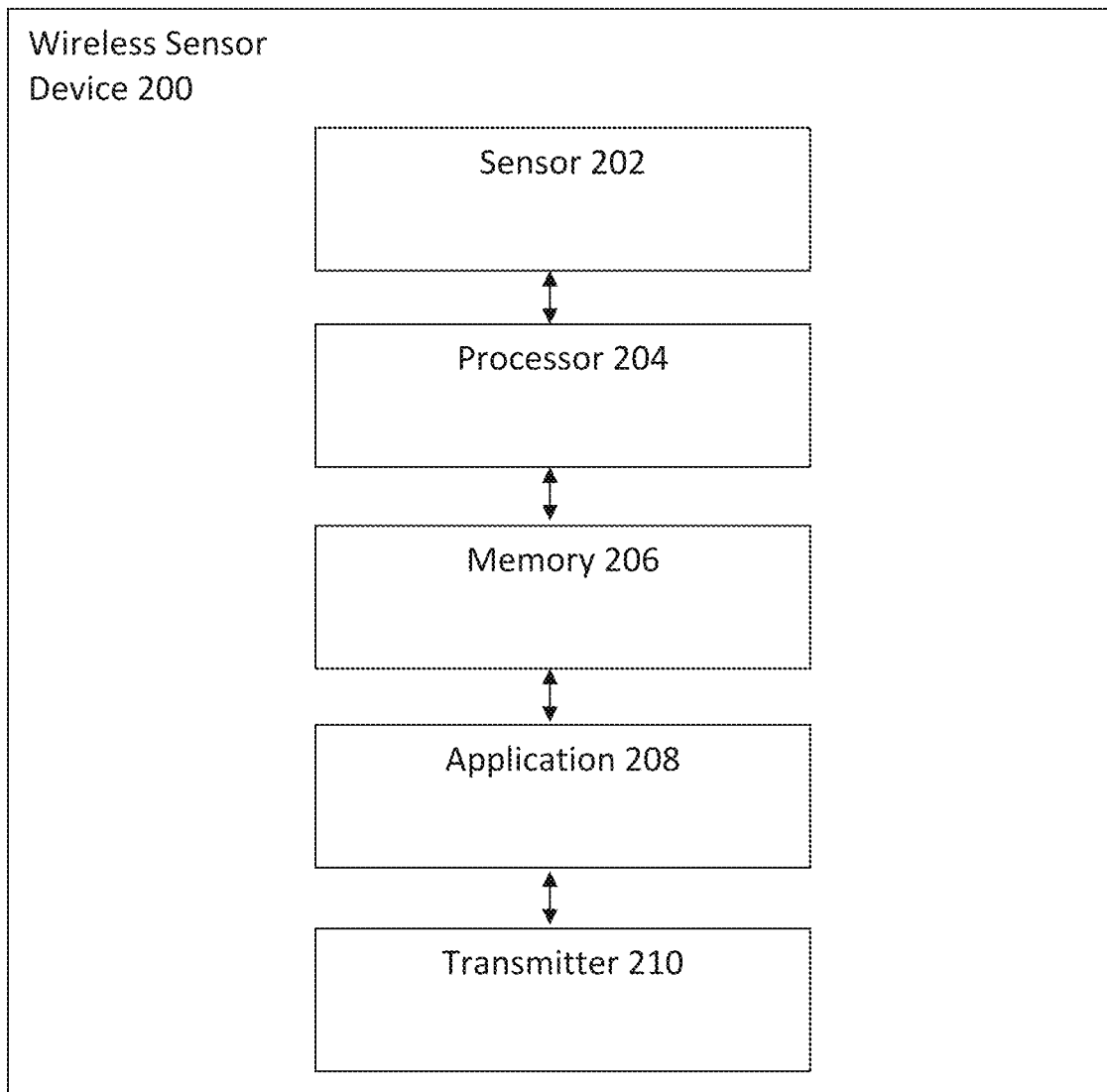
FIG. 2 illustrates a wireless sensor device in accordance with an embodiment.

FIG. 2 illustrates a wireless sensor device 200 in accordance with an embodiment. The wireless sensor device 200 includes a sensor 202, a processor 204 coupled to the sensor 202, a memory 206 coupled to the processor 204, an application 208 coupled to the memory 206, and a transmitter 210 coupled to the application 208. The wireless sensor device 200 is attached, in any orientation, to a user. The sensor 202 obtains data from the user and transmits the data to the memory 206 and in turn to the application 208. The processor 204 executes the application 208 to determine information regarding an ECG of the user and to subsequently determine a respiratory rate of the user. The information is transmitted to the transmitter 210 and in turn relayed to another user or device.

One of ordinary skill in the art readily recognizes that the wireless sensor device 200 can utilize a variety of devices for the sensor 202 including but not limited to uni-axial accelerometers, bi-axial accelerometers, tri-axial accelerometers, gyroscopes, pressure sensors, photoplethysmograph (pulse oximeter sensors), and electrodes and that would be within the spirit and scope of the present invention. One of ordinary skill in the art readily recognizes that the wireless sensor device 200 can utilize a variety of devices for the processor 204 including but not limited to microprocessors, controllers, and microcontrollers and that would be within the spirit and scope of the present invention. In addition, one of ordinary skill in the art readily recognizes that a variety of devices can be utilized for the memory 206, the application 208, and the transmitter 210 and that would be within the spirit and scope of the present invention.

One of ordinary skill in the art readily recognizes that the information regarding an ECG of the user can be different types of information including but not limited to an ECG data signal segment and that would be within the spirit and scope of the present invention. Additionally, one of ordinary skill in the art readily recognizes that the ECG data signal segment can be measured at a variety of sampling frequencies and predetermined time periods including but not limited to a 125 Hz sampling frequency ($F_s$) and a predetermined time period length of 40 seconds and that would be within the spirit and scope of the present invention.

Figure 3:
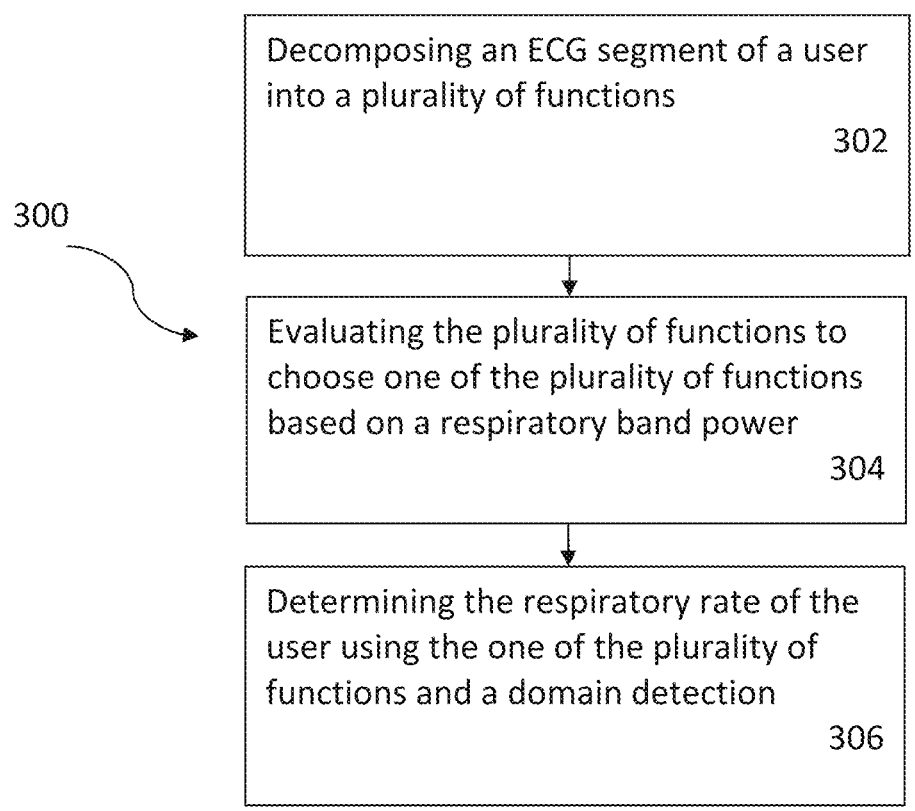
FIG. 3 illustrates a flow chart of a method in accordance with an embodiment.

FIG. 3 illustrates a flow chart of a method 300 in accordance with an embodiment. Referring to FIGS. 2 and 3 together, an ECG segment of a user measured by the sensor 202 is decomposed into a plurality of functions by the application 208, via step 302. Each of the plurality of functions is evaluated by the application 208 to choose one of the plurality of functions based on a respiratory band power, via step 304. The respiratory rate is determined by the application 208 using the one of the plurality of functions and a domain detection, via step 306. One of ordinary skill in the art readily recognizes that the application 208 can be different types of executable applications and that would be within the spirit and scope of the present invention.

One of ordinary skill in the art readily recognizes that before the ECG segment measured by the sensor 202 is decomposed into a plurality of functions by the application 208, it can be pre-processed to eliminate noise and artifacts utilizing a variety of mechanisms including but not limited to using any combination of a low pass digital filter with a cutoff frequency ($F_c$) of 10 Hz and a down sampling with a $F_s$ of 25 Hz and that would be within the spirit and scope of the present invention.

In one embodiment, the ECG signal segment x(t) is decomposed into a plurality of Intrinsic Mode Functions (IMFs) using an Ensemble Empirical Mode Decomposition (EEMD) algorithmic process. Empirical mode decomposition (EMD) is a nonlinear, adaptive time-frequency analysis technique and is a fully data driven tool that decomposes an original signal into fast/high and slow/low oscillations/ frequencies in decreasing fashion. The EMD algorithm decomposes a given ECG signal segment x(t) into a set of zero-mean amplitude modulation (AM) and frequency modulation (FM) components called Intrinsic Mode Functions (IMFs) or oscillatory modes. Each IMF is defined as a function that must satisfy two conditions: a) in the whole data set, |(#of Extrema)−(#of Zeroes)|<=1, and b) at any time point of the signal, the mean value of max envelope and min envelope is zero. The EMD algorithm is represented by the following equation, where $d_k(t)$ is the IMF, K is the number of modes, r(t) is a residual trend, and k=1, 2 ... K:

$$x(t)=\Sigma(d_k(t)+r(t)), \text{where } \Sigma \text{ is from } k=1 \text{ to } K.$$

One of ordinary skill in the art readily recognizes that the EMD algorithm experiences mode mixing that is eliminated utilizing EEMD and that would be within the spirit and scope of the present invention. EEMD is a noise-assisted data analysis method that determines the true IMF components as the mean of a number of ensemble trials in which the signal is added with white noise of finite amplitude. The different realizations of white noise cancel each other out in time-space ensemble mean. Therefore, only the true IMF components of ECG signal segment x(t) survive in the white noise-added signal ensemble mean.

Additionally, one of ordinary skill in the art readily recognizes that the amplitude of the added white noise, the number of ensemble trials (or realization index), and number of sifting operations can be a variety of selections including but not limited to 0.2*standard deviation of the signal for the amplitude of the added white noise, 100 for the number of ensemble trials, and 10 for the number of sifting operations and that would be within the spirit and scope of the present invention.

In this embodiment, the EEMD algorithmic process adds white noise $w_i(t)$ to the target ECG segment data x(t) to produce a new signal $x_i(t)$ represented by the following equation:

$$x_i(t)=x(t)+w_i(t), \text{where } i \text{ is the realization index}(i=1, \ldots ,100).$$

Let j=k=0, $h_{i,j,k}(t)=x_i(t)$, and $r_{i,k}(t)=x_i(t)$. The signal $h_{i,j,k}(t)$ is decomposed using EMD which includes the steps of: a) identifying all the extrema (minima and maxima) of $h_{i,j,k}(t)$, b) obtaining the respective envelopes $e_{min}(t)$ and $e_{max}(t)$ via cubic spline interpolation, c) computing the mean envelope $m(t)=((e_{min}(t)+e_{max}(t))/2$, d) extracting the detail $h_{i,j+1,k}(t)=h_{i,j,k}(t)-m(t)$, and repeating the above steps a-d on $h_{i,j+1,k}(t)$ with j←j+1 until j=9 (e.g., 10 repetitions); each repeat is known as a sifting operation. One of ordinary skill in the art readily recognizes that the above steps a-d can be repeated a different number of times and that would be within the spirit and scope of the present invention.

In step e), each effective IMF is determined as $d_{i,k+1}(t)=h_{i,10,k}(t)$ where $h_{i,10,k}(t)$ is the extracted detail. In step f), the residual $r_{i,k+1}(t)$ is obtained by subtracting this effective IMF from the new signal as represented by the following equation: $r_{i,k+1}(t)=r_{i,k}(t)-d_{i,k+1}(t)$. In step g) set j=0, consider the new input signal $h_{i,j,k+1}(t)=r_{i,k+1}(t)$, set k←k+1, and repeat steps a to f. The steps a to f are repeated K times (e.g., k=0, ... , K−1) where K=$\log_2(N)$−1 and N is the length of the data. As a result, the respective IMFs $d_{i,k}(t)$ and residues $r_{i,k}(t)$, k=1, . . . , K for each realization i are obtained. In step h) the realization index 'i' is incremented (i←i+1) and the indexes j and k are reset (j=0, k=0). The above-mentioned steps a-g are then repeated until i=100. As a result of this process, the following signals are generated: noisy ECG signals $x_i(t)$, where i=1, . . . , 100, noisy IMFs $d_{i,k}(t)$, and noisy residues $r_{i,k}(t)$, where i=1, . . . , 100 and k=1, . . . , K. Finally, the true IMFs $d_k(t)$ and residue $r_k(t)$ are determined by calculating the ensemble means of $d_{i,k}(t)$ and $r_{i,k}(t)$ per the following equations:

$$d_k(t) = \frac{1}{100}\sum_{i=1}^{100} d_{i,k}(t) \text{ and } r(t) = \frac{1}{100}\sum_{i=1}^{100} r_{i,K}(t).$$

In one embodiment, once a plurality of true IMFs are determined, the spectral content of each of the plurality of true IMFs is evaluated by obtaining a Power Spectral Density (PSD) for each of the plurality of true IMFs. In one embodiment, the PSD is obtained using the Welch periodogram algorithm. The respiratory band power for each of the plurality of true IMFs is obtained as the area under the PSD curve between certain frequencies (e.g., frequencies from 0.11 Hz to 0.45 Hz). One of ordinary skill in the art readily recognizes that the respiratory band power obtained for each of the plurality of IMFs can be a variety of ranges including but not limited to a range between 0.11 Hz to 0.45 Hz and that would be within the spirit and scope of the present invention.

The total respiratory band power is obtained as the sum of each IMF's respiratory band power. Then the ratio of individual respiratory band power to the total respiratory band power is obtained as a percentage. Finally, the specific true IMF that contributes maximal percentage of the total respiratory band power of the plurality of true IMFs is selected as a surrogate respiration waveform.

Using the specific true IMF that is selected as the surrogate respiration waveform, the breath-to-breath respiratory rate of the user is determined in the time-domain as (1/respiration interval in seconds×60) using an algorithm that can identify peak events with the computation of a first derivative of the surrogate respiration waveform and can find the zero crossing events with positive to negative sign change. One of ordinary skill in the art readily recognizes that this time-domain based algorithm can be a variety of algorithmic forms and that would be within the spirit and scope of the present invention.

Figure 7:
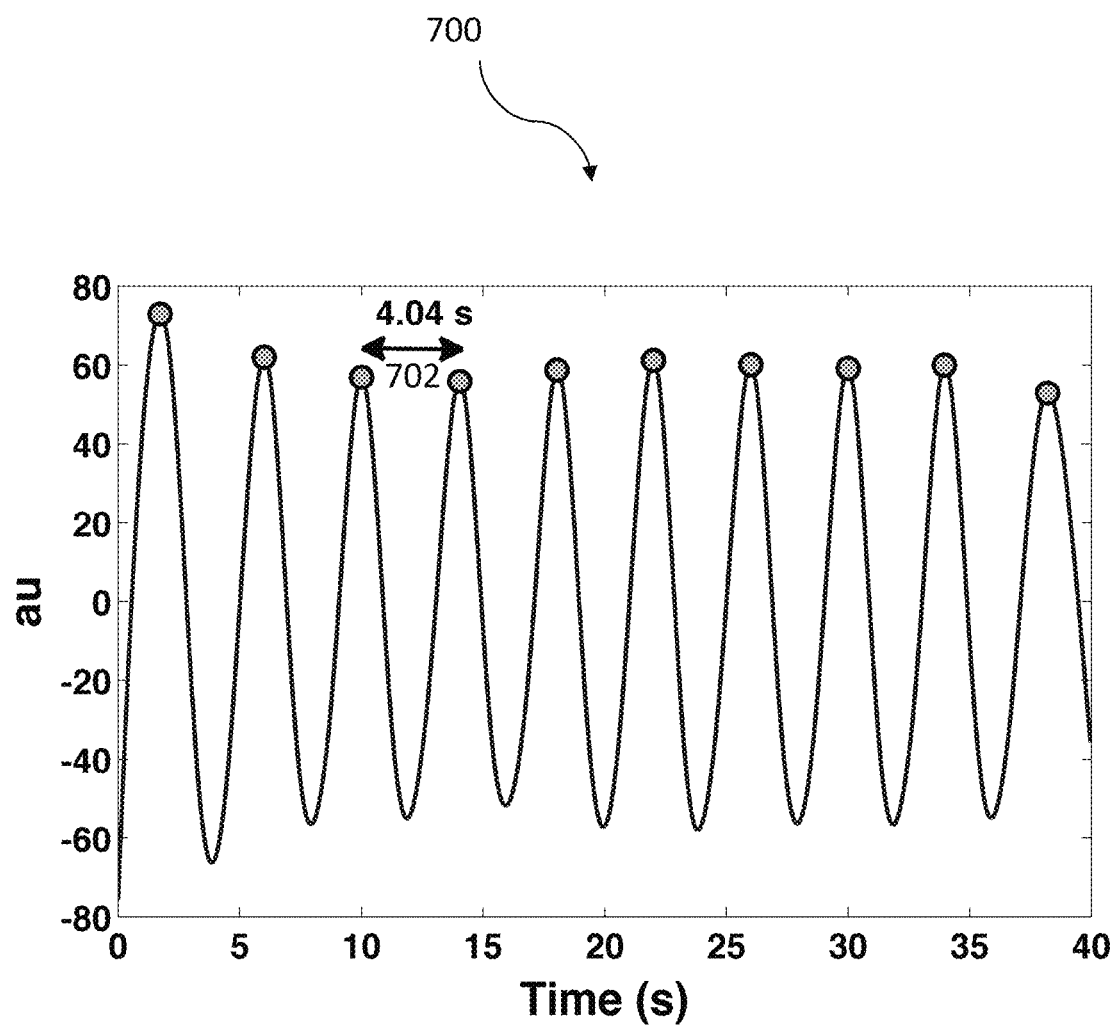
FIG. 7 illustrates a diagram of a time-domain based peak detection algorithm in accordance with an embodiment.

FIG. 7 illustrates a diagram 700 of a time-domain based peak detection algorithm that extracts breath-to-breath respiratory rates from the ECG decomposed respiratory surrogate waveform. In FIG. 7, the identified peak events in a sample ECG decomposed surrogate respiratory waveform are illustrated with black circles filled in green color. The time difference between two consecutive peaks, denoted by the arrow 702, is found to be a breathing time interval of 4.04 seconds which corresponds to (1/4.04)*60 or approximately 14.85 breaths per minute. From these breath-to-breath respiratory rates, the average respiratory rate can be found for a predetermined time period data window including but not limited to 40 seconds.

On the other hand, the average respiratory rate for the predetermined time period data window of 40 seconds in the current selection can be determined in the frequency-domain from the PSD of the surrogate respiration waveform by determining a peak frequency with a maximal PSD in the frequency band of 0.11 Hz to 0.45 Hz. In one embodiment, the ECG signal segment is shifted every 5 seconds to provide a 35 second overlap for increased precision in determining the respiratory rate. One of ordinary skill in the art readily recognizes that a variety of shifting times can be utilized and that would be within the spirit and scope of the present invention.

Figure 4:
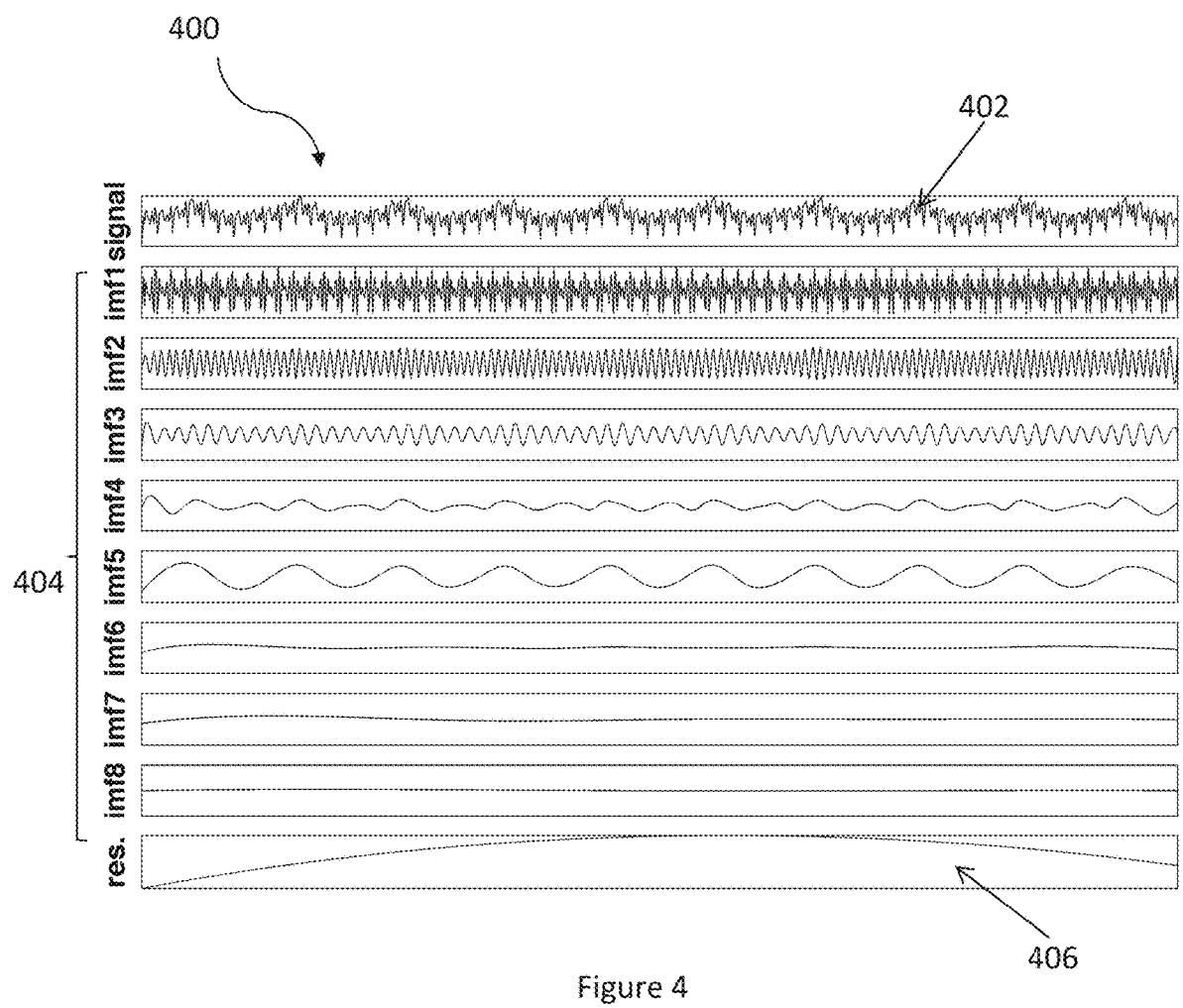
FIG. 4 illustrates a diagram of a decomposition of the ECG in accordance with an embodiment.

FIG. 4 illustrates a diagram 400 of a decomposition of the ECG in accordance with an embodiment. The diagram 400 includes an ECG segment 402 that is low pass filtered with a cutoff frequency of 10 Hz and later resampled at 25 Hz, a plurality of true IMFs 404, and a residual 406 obtained utilizing the aforementioned EEMD decomposition algorithmic process. One of ordinary skill in the art readily recognizes that although 8 true IMFs are calculated, a variety of different number of true IMFs can be calculated based on the length of the predetermined time period data window to be analyzed and that would be within the spirit and scope of the present invention.

One of ordinary skill in the art readily recognizes that a variety of comparative data sets can be formulated to compare respiratory rate signals that have been determined by conventional methods to the respiratory rate signals that have been determined by the present invention and that would be within the spirit and scope of the present invention. Additionally, one of ordinary skill in the art readily recognizes that the respiration rate detection algorithm can be applied to short-term (e.g., a few minutes to a few hours) as well as long-term (e.g., a 24 hour period to a few days) ECG monitoring applications and that would be within the spirit and scope of the present invention.

Figure 5:
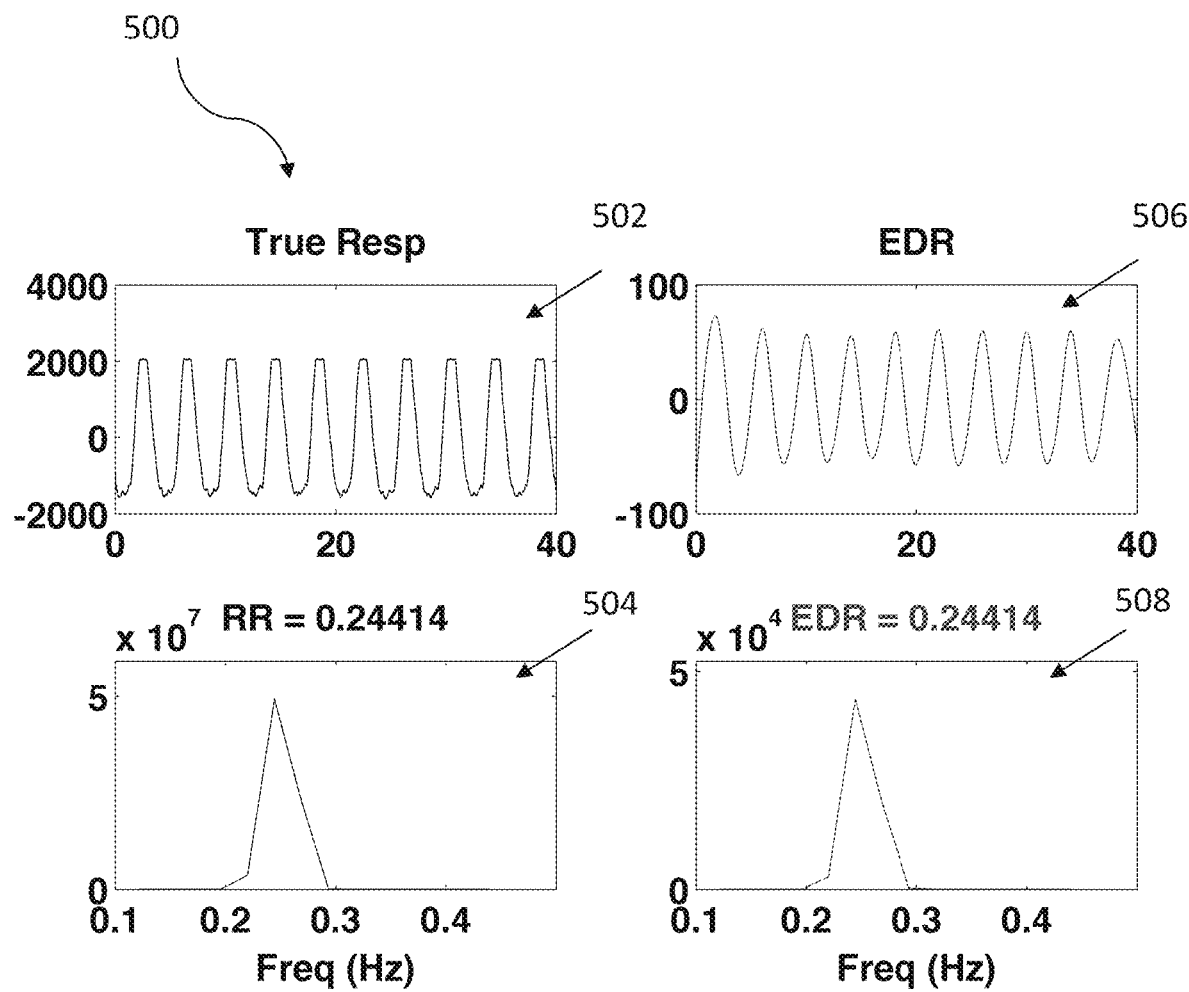
FIG. 5 illustrates a diagram of a comparison between a true respiration signal and ECG decomposed respiration signal in accordance with an embodiment.

FIG. 5 illustrates a diagram 500 of a comparison between a true respiration signal and ECG decomposed respiration signal in accordance with an embodiment. The diagram 500 includes a data set 502 displaying a true respiration signal, a data set 504 displaying that the true respiration signal's frequency was determined to be 0.244 Hz from PSD, a data set 506 displaying an ECG decomposed respiration (EDR) signal obtained by the present invention, and a data set 508 displaying that the EDR signal's frequency was also determined to be 0.244 Hz. Accordingly, the EDR signal's frequency was determined to be the same as the true respiration signal's frequency. As shown in FIG. 5, the peak frequency with the maximal PSD in the frequency band of 0.11 Hz to 0.45 Hz is found to be 0.244 Hz which correspond to approximately 14.65 breaths/min.

Figure 6:
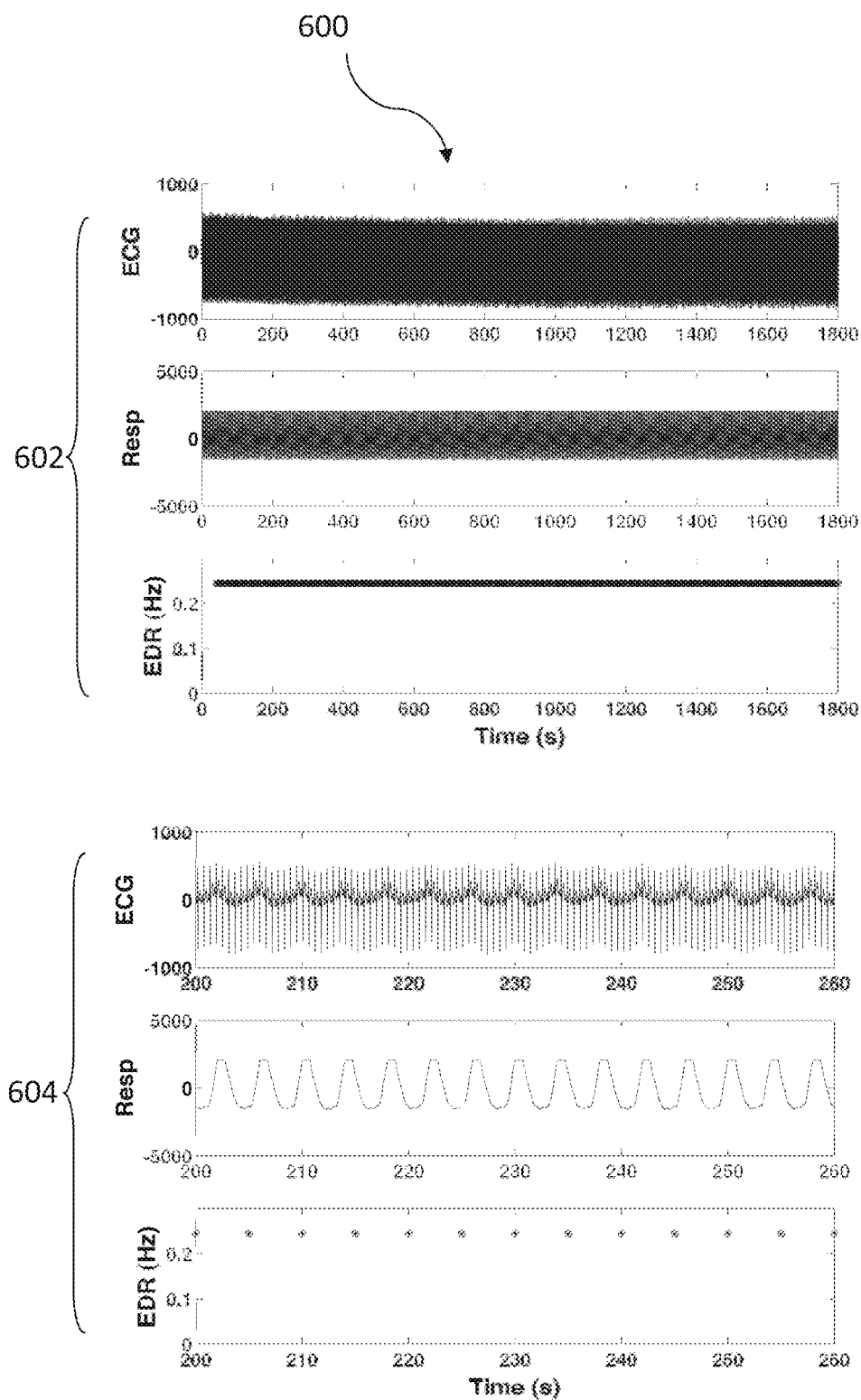
FIG. 6 illustrates a diagram of respiratory rate extraction in accordance with an embodiment.

FIG. 6 illustrates a diagram 600 of respiratory rate extraction in accordance with an embodiment. The diagram 600 includes a data set 602 displaying the ECG data, the respiration data, and the frequency values of a respiration rate extraction for data compiled over a 30 minute period and a zoomed in view 604 of the data set 602 that spans a 1 minute period and that shows 100% accuracy of the EDR signal obtained by the present invention.

As above described, the method and system allow for determining a respiratory rate of a user using an electrocardiogram (ECG) segment of the user. By attaching a wireless sensor device to the user to measure a data signal representing an ECG segment, processing the resultant data signal, decomposing the processed signal into Intrinsic Mode Functions (IMFs), and evaluating these IMFs based upon a spectral content of the respiratory band power, an accurate respiratory rate of the user can be calculated utilizing a non-invasive and efficient system.

A method and system for determining a respiratory rate of a user using an electrocardiogram (ECG) segment of the user has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method to determine a respiratory rate of a user using a wireless sensor device that includes at least one electrode, a processor, a transmitter and a memory device coupled to the processor, the memory device stores executable instructions that, when executed by the processor, causes the processor to perform operations, comprising:
   measuring an electrocardiogram (ECG) segment of the user via the at least one electrode;
   decomposing the ECG segment into a plurality of Intrinsic Mode Functions (IMFs) using Ensemble Empirical Mode Decomposition (EEMD);
   evaluating the plurality of IMFs to choose one of the plurality of IMFs based on a respiratory band power of the plurality of IMFs;
   evaluating spectral content of each of the plurality of IMFs by obtaining a Power Spectral Density (PSD) for each of the plurality of IMFs;
   obtaining the respiratory band power for each of the plurality of IMFs;
   choosing one of the plurality of IMFs that contributes maximal percentage of a total respiratory band power of the plurality of IMFs;
   providing the one of the plurality of IMFs as a surrogate respiration waveform; and
   determining the respiratory rate using the one of the plurality of functions and a time-domain based peak detection algorithm.

2. The method of claim 1, wherein the determining further comprises:
   determining the respiratory rate using breath-to-breath peak detection in time-domain and respiratory frequency peak in the PSD of the surrogate respiration waveform.

3. The method of claim 2, wherein the breath-to-breath peak detection in time-domain includes an algorithm that identifies peak events by computing a first derivative of the surrogate respiration waveform and finds zero crossing events with positive to negative sign changes.

4. The method of claim 1, wherein the PSD is obtained using a Welch periodogram.

5. The method of claim 1, wherein the respiratory band power obtained for each of the plurality of IMFs is an area under the PSD between frequencies 0.11 Hz to 0.45 Hz.

6. The method of claim 1, further comprising:
   processing the ECG segment using both a low pass digital filter with a cutoff frequency ($F_c$) of 10 Hz and a down sampling with a sampling frequency ($F_s$) of 25 Hz.

7. The method of claim 1, wherein the ECG segment is measured at a 125 Hz sampling frequency ($F_s$) and at a length of 40 seconds.

8. The method of claim 7, further comprising:
   shifting the ECG segment every 5 seconds to provide a 35 second overlap for determining the respiratory rate.

9. A non-transitory computer-readable medium storing executable instructions that, in response to execution, cause a wireless sensor device that includes at least one electrode, a processor, a transmitter and a memory device coupled to the processor, to perform operations to determine a respiratory rate of a user using an electrocardiogram (ECG) segment of the user comprising:
   measuring an electrocardiogram (ECG) segment of the user via the at least one electrode;
   decomposing the ECG segment into a plurality of Intrinsic Mode Functions (IMFs) using Ensemble Empirical Mode Decomposition (EEMD);
   evaluating the plurality of IMFs to choose one of the plurality of IMFs based on a respiratory band power of the plurality of IMFs;
   evaluating spectral content of each of the plurality of IMFs by obtaining a Power Spectral Density (PSD) for each of the plurality of IMFs;
   obtaining the respiratory band power for each of the plurality of IMFs;
   choosing one of the plurality of IMFs that contributes maximal percentage of a total respiratory band power of the plurality of IMFs;
   providing the one of the plurality of IMFs as a surrogate respiration waveform; and
   determining the respiratory rate using the one of the plurality of functions and a time-domain based peak detection algorithm.

10. The non-transitory computer-readable medium of claim 9, wherein the determining further comprises:
    determining the respiratory rate using breath-to-breath peak detection in time-domain and respiratory frequency peak in the PSD of the surrogate respiration waveform.

11. The non-transitory computer-readable medium of claim 10, wherein the breath-to-breath peak detection in time-domain includes an algorithm that identifies peak events by computing a first derivative of the surrogate respiration waveform and finds zero crossing events with positive to negative sign changes.

12. The non-transitory computer-readable medium of claim 9, wherein the PSD is obtained using a Welch periodogram.

13. The non-transitory computer-readable medium of claim 9, wherein the respiratory band power obtained for each of the plurality of IMFs is an area under the PSD between frequencies 0.11 Hz to 0.45 Hz.

14. The non-transitory computer-readable medium of claim 9, further comprising:
  processing the ECG segment using both a low pass digital filter with cutoff frequency ($F_c$) of 10 Hz and a down sampling with a sampling frequency ($F_s$) of 25 Hz.

15. The non-transitory computer-readable medium of claim 9, wherein the ECG segment is measured at a 125 Hz sampling frequency ($F_s$) and at a length of 40 seconds.

16. The non-transitory computer-readable medium of claim 15, further comprising:
  shifting the ECG segment every 5 seconds to provide a 35 second overlap for determining the respiratory rate.

* * * * *